United States Patent [19]

Hillion et al.

[11] Patent Number: 5,880,298

[45] Date of Patent: Mar. 9, 1999

[54] PROCESS FOR OLIGOMERIZATION OF POLYUNSATURATED ACIDS AND ESTERS, PRODUCTS OBTAINED AND USE THEREOF

[75] Inventors: Gerard Hillion, Herblay; Robert Stern, Paris; Odile Le Borgne, Nanterre, all of France

[73] Assignees: Institut Francais du Petrole, Cedex; Onidol, Rueil Malmaison, both of France

[21] Appl. No.: 186,483

[22] Filed: Jan. 14, 1994

[30] Foreign Application Priority Data

Jan. 18, 1993 [FR] France .................................. 93 00505

[51] Int. Cl.$^6$ ............................... C09F 7/00; C07B 35/08
[52] U.S. Cl. .............................. 554/26; 554/28; 554/126; 560/127; 560/190; 560/202
[58] Field of Search .................... 560/202, 190, 560/127; 554/26, 28, 126, 161, 163, 165

[56] References Cited

U.S. PATENT DOCUMENTS

| | | | |
|---|---|---|---|
| 2,793,219 | 5/1957 | Barrett et al. | 260/407 |
| 2,793,220 | 5/1957 | Barrett et al. | 260/407 |
| 3,162,658 | 12/1964 | Baltes et al. | 554/126 |
| 3,417,130 | 12/1968 | Pruett et al. | 554/126 |
| 4,032,550 | 6/1977 | White et al. | 554/163 |
| 4,195,000 | 3/1980 | Charles et al. | 260/22 D |
| 4,776,983 | 10/1988 | Hayes | 260/407 |
| 5,106,541 | 4/1992 | Fristad et al. | 554/213 |

FOREIGN PATENT DOCUMENTS 1159735  7/1969  United Kingdom .

OTHER PUBLICATIONS

J.C. Cowan, "Dimer Acids," *J.A.O.C.S.*, vol. 39, 1962, pp. 534–545.

*Primary Examiner*—Marianne M. Cintins
*Assistant Examiner*—Dwayne C. Jones
*Attorney, Agent, or Firm*—Millen, White, Zelano, & Branigan, P.C.

[57] ABSTRACT

For the oligomerization of a fatty ester or fatty acid containing conjugated double bonds, the reaction uses a catalyst consisting of an activated earth, e.g., montmorillonite, at a temperature of from 100°–180° C., preferably from 130°–160° C. The process can be carried out continuously or in a batch process on a fixed bed and is particularly applicable to conjugated methyl esters obtained by conjugating and transesterifying sunflower seed oil. The oligomerized products obtained are particularly useful as lubricants or polycondensation reactants.

41 Claims, No Drawings

PROCESS FOR OLIGOMERIZATION OF POLYUNSATURATED ACIDS AND ESTERS, PRODUCTS OBTAINED AND USE THEREOF

BACKGROUND OF THE INVENTION

The present invention relates to a novel process for oligomerization of fatty esters and acids of polyunsaturated oils. More precisely, it is concern with a process for the production of dimers and trimers at low temperatures and with small quantities of catalyst from any polyunsaturated ester or acid whose double bonds are conjugated or conjugatable.

Dimers or trimers obtained from acids or esters may be used as base materials in the production of lubricants, polyamide monomers, amide type anticorrosive agents, or paint additives.

The preparation of fatty acid dimers or oligomers from monoenyl, dienyl or trienyl fatty esters or acids is known. Activated earths (also called "activated clays") containing various additives (water, acid, chlorinated derivative, lithium salt, etc.) are currently employed as catalysts. British patent document GB 2 172 597 and the article published by J C COWAN in J.A.O.C.S. Vol 39, 1962, pages 534–545, describe the syntheses. The disadvantages of this technique are known. The reaction requires from 6 to 10% by weight of activated earth with respect to the product to be oligomerized and this earth is lost. Temperatures of 220° to 250° C. and reaction times of 6 to 8 hours are required. Filtration is difficult. When starting from polyenyl structures, the products obtained are in part aromatic. The cloud point of these compounds produced from a polyenyl acid is not very low. It is thus preferred to use monoenyl extracts of tallow. Finally, the resulting acidity when starting from esters is often high, whatever the ester employed.

Lubricant bases cannot be manufactured using this synthesis. Fatty acids form by ester hydrolysis which necessitates that the fatty acids be esterified before any hydrogenation that may be required. In addition, the monomers must be distilled off since not only do these monomers have low molecular weights but, even in the absence of hydrogenation, a large quantity of saturated derivatives is also produced during the course of the reaction. The esters of the dimers and oligomers are then transesterified with a higher alcohol if starting from methyl esters. The manufacture of a lubricant base is thus a relatively lengthy process, and it would be of advantage to simplify the process.

The literature records attempts to manufacture diners or oligomers at low temperature (120°–180° C.) (French patent FR 2 202 874). However, the process used does not appear to be very attractive. The ion exchange resin used, which is only active towards dienes and trienes, gives rise to a significant amount of ester hydrolysis despite the relatively low temperature (130°–140° C.), bringing the acidity to acid values which may reach from 12 to 30. The product obtained is quite colored and the resin rapidly loses activity. Finally, the dimer/trimer weight ratio is close to 1, while a good value generally obtained with activated earths is on the order of 4 to 5. Dimers rather than trimers are in demand for numerous applications.

In one example in the literature, low temperature oligomerization of fatty acid esters is effected using almost 10% by weight of activated earth; however, in this instance the esters of very rare oils are used, such as esters of China wood oil or oiticica oil (British patent document GB-A 1 466 418). These esters are double bonded trienes with trans-configurations. These structures are deemed to be very polymerizable.

Finally, German patent document DE 1 268 616 mentions the use of conjugated polyunsaturated esters in a co-oligomerization reaction of esters and coumarone or indene in the presence of activated earths between 40° and 180° C. In this patent document, it is indicated that there is no homopolymerization of the conjugated esters since the saponification values of the products which are not monomers, after distillation, are very different from those of the dimers.

SUMMARY OF THE INVENTION

The invention, which differs from the prior art describing the use of activated earths on non-conjugated esters and at high temperature, proposes the use of an activated earth in the presence of polyunsaturated conjugated esters or acids (or which have been conjugated, for example, by an alkaline route) at a lower temperature. The compositions produced are particularly interesting, in particular as lubricant bases. The technique of the invention also has the advantage of being easier to carry out.

Surprisingly, the reactivity of the conjugated esters does not appear to have excited the interest of those using activated earths, who have not detected the novel properties of the products formed under these conditions, nor the economic advantages which this technique represents.

Because of the combined use of conjugated compounds as base material and activated earth as catalyst, it is possible to dimerize in less time at a lower temperature using less earth, but above all to operate continuously to produce a particularly advantageous dimer.

The invention thus provides a process for oligomerization of at least one fatty ester of a 1 to 12 carbon atom alkyl or at least one fatty acid to produce a mixture comprising mainly dimers and trimers, the process being characterized in that the starting ester or acid containing conjugated double bonds (or bonds which have been conjugated) is brought into contact with an activated earth at a temperature of 100° to 180° C., preferably 130° to 160° C.

Polyunsaturated fatty acids and polyunsaturated alkyl fatty esters to be considered are generally mixtures corresponding to natural, vegetable or animal, predominantly polyunsaturated oils or fats, derived therefrom by transesterification (for example, by basic catalysis) by means of an aliphatic monoalcohol having 1 to 12 carbon atoms (for the esters) or by hydrolysis (for the acids). The esters and acids under consideration may have, for example, from 12 to 22 carbon atoms in their acid portions. The mixtures of acids and esters used thus comprise polyunsaturated chains with, for example, 2 or 3 ethylene bonds of which some may be conjugated or conjugatable, as well as monounsaturated or saturated chains. Preferably, mixtures are used wherein the esters or acids have mainly polyunsaturated chains.

Examples of polyunsaturated esters or acids with conjugated or conjugatable double bonds are those extracted from fish oils, sunflower seed oils, safflower oil, soya oil, linseed oil, tobacco oil, corn oil, grape seed oil, or any oil containing polyunsaturated compounds.

The process of the invention advantageously uses as a starting material a methyl ester or the ester of a higher alcohol such as, for example, a high alcohol which may be used, as will be shown below, to transesterify the mixtures produced by the inventive process when the residual monomers are not separated out and when it is nevertheless desirable to use the product as a lubricant base. When the unconverted monomers are separated out of the reaction mixture, it is preferable to use esters of low molecular weight alkyls, for example having 1 to 4 carbon atoms.

In the description that follows, a high alcohol is intended to mean a monofunctional or difunctional alcohol with an aliphatic chain which contains a larger number of carbon atoms than the alkyl group of the starting ester. Depending on the case, the high alcohol may be selected from butanol, 2-ethylhexanol, C7 or C13 oxo alcohols, diols such as ethyleneglycol, neopentylglycol, propyleneglycol, etc.

The proportion of dimers in the product obtained is generally greater than that of the trimers. The product may also contain unreacted monomers.

The ester dimer obtained is less acid, in general AV<6 (AV=acid value). The yield may be greater than 60% in the case of conjugated methyl esters from sunflower seed. The remaining monomer contains few saturated derivatives and it is possible in certain cases to obtain, for certain uses, mixtures of monomers, dimers and oligomers with a sufficient viscosity and very low cloud point without the need to distill the monomers. In the prior art, when activated earths are used with monoenyl esters at high temperatures, crystallizable saturated compounds may be formed which have to be separated out.

If the monomers are distilled off in the process of the invention, a very clear mixture of dimers and trimers is obtained which can readily be transesterified, and whose initial acid value (AV) is low, for example less than 6.

When it is desired to use the inventive process to manufacture a lubricant, distillation of the monomers is also unnecessary and after transesterification with a high alcohol, a fairly stable oil can be produced.

The higher the proportion of polyunsaturated acids or esters in the starting substrate, the greater the conversion. Furthermore, conjugation of dienes or trienes is generally effected by different methods, for example with potassium alcoholates for esters, or with hot soda for fatty acids.

It should be noted that if the monomers are not distilled off following dimerization, the conjugation catalyst can be used to transesterify the starting methyl esters with a high alcohol, followed by dimerization of the high esters.

More specifically, in the inventive process a montmorillonite based activated earth catalyst is used. This earth has generally been treated with mineral acids. Many of these earths are used commercially as bleach bases and are extremely inexpensive. Additives may be combined with these earths (water, alcohol, magnesium or lithium salt, organic acid or sulphuric acid). Tonsil, Prolit, K10, etc (registered trademarks) are examples of commercial names of such earths.

The earths may be used in microsphere form, pellet form, or as extrusions, all of which are of use in a continuous process. Because of the relatively low operating temperature, fairly long lifetimes are possible. If the catalyst becomes deactivated, it can be reactivated by passage of an inert solvent, such as an aliphatic or cycloaliphatic hydrocarbon.

The inventive process may be carried out continuously or in a batch process.

In the continuous process, the conjugated ester or acid is generally passed one or more times through a column heated to 100°–180° C., more particularly to 130°–160° C., generally at a flow rate of from 1 to 5 volumes of ester or acid per volume of catalyst per hour (VVH=1 to 5). At the exit, filtration is carried out if required and transesterification is effected using a high alcohol, or the monomers are first distilled off and then transesterification is carried out. The monomers are mainly constituted by esters of oleic acid and saturated acids which are present at startup. The saturated derivatives could be first eliminated and the dienes concentrated by crystallization of the least unsaturated fatty acids or esters from methyl alcohol, acetone or hexane.

The monomer fraction distilled off may have a number of uses, including use as a substrate for subsequent dimerization under different conditions. Ideally, however, the monoenes should be transformed into dienes by dehydrogenation.

The batch process consists in mixing the conjugated ester or acid and activated earths and heating for the required time to effect conversion. The reaction time is generally from 1 h to 4 h.

The temperatures are generally between 100° and 180° C., preferably 130° to 160° C. Concentrations are generally from 1 to 10% by weight, preferably from 1 to 4% by weight, of activated earth with respect to the substrate to be oligomerized.

At the end of the reaction, either the mixture of monomers, dimers and trimers is used, or the monomers are separated out, for example by distillation. As indicated above, transesterification may be carried out using a high alcohol.

The following examples illustrate the invention but are not limiting. Example 3 is given by way of comparison.

EXAMPLE 1

8 g of Tonsil FF activated earth was added to 200 g of the methyl ester of sunflower seed oil containing 62% of cis-trans conjugated linoleic ester. The mixture was heated with stirring to 135° C. in an argon atmosphere. After 1 hour of reaction the following uncorrected values were obtained (in weight %) using gel permeation liquid chromatography (GPC):

| | |
|---|---|
| Trimers and + | 19.5 weight % |
| Dimers | 47.2 weight % |
| Monomers | 34.3 weight % |

Conversion was the same after 4 h. Flash distillation at 205° C. under vacuum gave 51% by weight of monomers. Analysis of these monomers showed the presence of 19.2% by weight of conjugated dienes still capable of being transformed into dimers and 3.4% by weight of linoleic acid, the remainder being monoenes and saturated esters. The dimer acidity was low, of the order of 2.9% by weight; that of the substrate before distillation being 2.7% by weight.

EXAMPLE 2

The same example was effected under a vacuum of 15 mm of mercury ($2.10^3$ Pa) using a filter pump. The following results were obtained using GPC analysis (gel permeation liquid chromatography). The values given are uncorrected, (% by weight):

| | Monomers | Dimers | Trimers |
|---|---|---|---|
| 1 h | 36% | 48% | 16% |
| 3 h | 31.5% | 48.5% | 19.6% |
| 4 h | 34.4% | 45.7% | 19.7% |
| 5 h | 34.7% | 45.3% | 19.9% |

Analysis of the monomers by CG (vapour phase chromatography) in weight % was as follows:

C$_{16}$:0 = 12.7%
C$_{18}$:0 = 7.6%
C$_{18}$:1 = 29.0%
C$_{18}$:2 unconj = 3.4%
butyl esters = 9.0%
C$_{18}$:2 conjugated = 21.0%
others = 17.3%

Oleic acidity was 2.1 weight % for the distilled monomers.

EXAMPLE 3

(comparison)

Treatment of the unconjugated methyl ester of sunflower seed oil under the same conditions as in example 1 resulted in no dimerization, even after 6 h at 135° C. using 4% by weight of activated earth.

EXAMPLE 4

1300 g of conjugated methyl esters of sunflower seed oil was heated with 52 g of montmorillonite type activated earth. At 150° C., the following results were obtained (weight %):

|  | Dimers + trimers |
|---|---|
| 1 h | 58.2% |
| 2 h | 63.8% |
| 3 h | 64.2% |

Uncorrected results using GPC.

After filtering using a no. 4 frit, a clear yellow product was obtained. The acidity was 3.7 weight %. Half of the product was set aside; the other half was distilled at 208° C. under a vacuum of 1–2 mm of mercury (1.33.10$^2$ to 2.67.10$^2$ Pa). From 600 g of starting substance, 301 g of a mixture of dimers and trimers was obtained. This product was transesterified using 2-ethylhexyl alcohol using a known technique, as was the undistilled product consisting of a mixture of monomers, dimers and trimers.

The following results were obtained:

|  | Monomers + Dimers + Trimers 2-ethylhexyl esters | Dimers + Trimers 2-ethylhexyl esters |
|---|---|---|
| viscosity, mm$^2$/s at: | | |
| 40° C. | 29.4 | 99.9 |
| 100° C. | 6.4 | 13.9 |
| viscosity index | 179 | 141 |
| flow point (°C.) | −24 | −51 |

The mixture containing monomers remained liquid above −24° C.

EXAMPLE 5

Conjugated methyl ester of sunflower seed oil was passed through a column filled with 20 cm$^3$ of granules of modified alkaline earth montmorillonite at an hourly rate of 20 cm$^3$ and at 150° C. The product obtained was partially converted. GPC gave 52.3% by weight of monomers, 24.3% by weight of dimers and 22.1% by weight of trimers. The catalyst was very stable. On repassing the product, the yield was increased to 60% by weight of a mixture of dimers/trimers; after passage of 1500 cm$^3$ of product, no drop in activity could be detected. This example shows the advantage of being able to operate at a lower temperature, since the catalyst is much more stable at this temperature. A clear yellow product exits. It has low acidity, no filtration is needed. Thus, using a 10 liter column, 240 liters of a mixture of monomers, dimers and trimers can be produced per day.

We claim:

1. A process comprising oligomerizing at least one C$_{12-22}$ fatty acid or at least one C$_{1-12}$-alkyl ester thereof, said acid or ester containing 2 or 3 conjugated double bonds, to produce a mixture containing mainly dimers and trimers, comprising contacting a starting material consisting essentially of said ester or acid containing conjugated double bonds with an activated earth at a temperature of 100° to less than 160° C.

2. A process according to claim 1, wherein the reaction temperature is 130° to less than 160° C.

3. A process according to claim 1, wherein said activated earth comprises montmorillonite.

4. A process according to claim 1, wherein the reaction is carried out as a batch process and is followed by filtration of the activated earth.

5. A process according to claim 4, wherein the activated earth is used at a concentration of 1 to 10% by weight with respect to the starting fatty ester or fatty acid.

6. A process according to claim 5 wherein the concentration is 1 to 4% by weight.

7. A process according to claim 1, wherein the reaction is continuous using a fixed bed column, and the fatty acid or ester is passed through the column at a flow ratio of 1 to 5 volumes of acid or ester per volume of catalyst.

8. A process according to claim 1, wherein the fatty acid portion or fatty acid part of the ester contains 12–22 carbon atoms.

9. A process according to claim 1, wherein the reaction temperature is 135° to 150° C.

10. An oligomerization process according to claim 1 conducted under vacuum.

11. An oligomerization process according to claim 1 conducted under a pressure of less than ten atmospheres.

12. A process according to claim 1, comprising transesterifying a mixture of fatty esters with a low molecular weight monoalcohol in the presence of a basic catalyst and conjugating at least part of the non-conjugated double bonds of the resultant low molecular weight alkyl ester mixture; then transesterifying the resultant conjugated ester mixture with a higher alcohol using the same basic catalyst; and oligomerizing the resultant transesterified ester mixture.

13. A process according to claim 1, wherein said at least one alkyl ester is at least one C$_1$–C$_4$ alkyl ester.

14. A process according to claim 13, wherein said at least one alkyl ester is at least one methyl ester.

15. A process according to claim 13, comprising transesterifying said at least one C$_1$–C$_4$ alkyl ester with an alcohol higher than the monoalcohol corresponding to said at least one C$_1$–C$_4$ alkyl ester and oligomerizing the resultant transesterified ester.

16. A process according to claim 1, comprising oligomerizing said at least on C$_1$–C$_4$ alkyl ester and transesterifying the resultant oligomerization product with an alcohol higher than the monoalcohol corresponding to said at least one C$_1$–C$_4$ alkyl ester.

17. A process according to claim 16, comprising separating by distillation remaining monomers before transesterifying the oligomerization product.

18. A process comprising a first step of subjecting at least one polyunsaturated fatty acid having 12–22 carbons atoms or at least one $C_{1-12}$ alkyl ester thereof, containing 2 or 3 non-conjugated double bonds, to a conjugation step to covert at least part of said non-conjugated double bonds to conjugated double bonds, and a second step of oligomerizing the resultant polyunsaturated fatty acid or ester containing conjugated double bonds in contact with activated earth at 100° to less than 160° C. to produce a mixture containing mainly dimers and trimers.

19. A process according to claim 18, wherein the double bonds in the starting fatty acid are conjugated by the action of a hot soda.

20. A process according to claim 18, wherein the double bonds in the starting fatty ester are conjugated by the action of a potassium alcoholate.

21. A process according to claim 18, wherein the double bonds of the starting fatty ester are conjugated during its preparation from a natural oil using a basic catalyst, said fatty ester being tranesterified with a monoalcohol higher than the monoalcohol corresponding to the at least one $C_{1-12}$-alkyl ester, using the same catalyst, then oligomerized.

22. A process according to claim 18, wherein said fatty acid or ester thereof subjected to said conjugation step is derived from sunflower seed oil.

23. A process according to claim 18, wherein said alkyl ester is at least on $C_1$–$C_4$ alkyl ester.

24. A process according to claim 23, wherein said at least one $C_1$–$C_4$ alkyl ester is at least one methyl ester.

25. A process according to claim 23, comprising conjugating said at least one $C_1$–$C_4$ alkyl ester in the presence of a basic catalyst, transesterifying the conjugated at least one $C_1$–$C_4$ alkyl ester obtained, with an alcohol higher than the monoalcohol corresponding to said at least one $C_1$–$C_4$ alkyl ester, in the presence of the same basic catalyst, and oligomerizing the resultant transesterified ester.

26. A process comprising: providing a natural oil containing fatty esters having non-conjugated double bonds; in the presence of a basic catalyst, transesterifying said ester with a monoalcohol higher than the monoalcohol corresponding to the fatter ester, in the presence of a basic catalyst, conjugating at least part of the non-conjugated double bonds of resultant ester; and oligomerizing the resultant transesterified and conjugated ester in contact with activated earth at 100° to less than 160° C. to produce a mixture of mainly dimers and trimers.

27. A process according to claim 26, wherein the natural oil contains a mixture of fatty esters of glycerol.

28. An oligomerization product produced by a process comprising oligomerizing at least one $C_{16-22}$ fatty acid or at least one $C_{1-12}$-alkyl ester thereof, said acid or ester being polyunsaturated and containing conjugated double bonds, to produce a mixture containing mainly dimers and trimers, by contacting a starting material consisting essentially of said polyunsaturated ester or acid, with an activated earth at a temperature of 100° to less than 160° C., whereby said oligomerization product contains carboxylic groups solely from said polyunsaturated ester or acid.

29. An oligomerization product according to claim 28, wherein said acid or ester contains 2 or 3 conjugated double bonds.

30. An oligomerization product according to claim 28, wherein the acid or ester was derived from a natural oil containing fatty esters containing non-conjugated double bonds which were conjugated in a preceding step.

31. An oligomerization product according to claim 30, wherein the natural oil is sunflower oil.

32. An oligomerization product according to claim 31, wherein remaining monomers have been distilled off.

33. An oligomerization product according to claim 31, wherein the product comprises a greater proportion of dimers than trimers.

34. An oligomerization product according to claim 33, wherein the product further comprises unreacted monomers.

35. An oligomerization product according to claim 31, wherein the activated earth consists essentially of montmorillonite.

36. An oligomerization product according to claim 28, wherein the activated earth consists essentially of montmorillonite.

37. An oligomerization product according to claim 28, wherein remaining monomers have been distilled off.

38. An oligomerization product according to claim 28, wherein the starting material was a methyl ester of sunflower seed oil containing cis-trans conjugated linoleic ester, and the resultant product contained 16–19.9% trimers; 45.3–48% dimers; and 31.5–36% of monomers.

39. An oligomerization product according to claim 28, wherein the starting material was conjugated methyl esters of sunflower seed oil and the resultant product which contained a mixture of dimers and trimers was transesterified with 2-ethylhexyl alcohol to produce a mixture of 2-ethylhexyl esters of the monomers, dimers and trimers having the following properties:

| viscosity, mm$^2$/s at: | |
| --- | --- |
| 40° C. | 29.4 |
| 100° C. | 6.4 |
| viscosity index | 179 |
| flow point (°C.) | −24. |

40. An oligomerization product according to claim 39, wherein the monomers are removed so as to obtain a mixture consisting essentially of 2-ethylhexyl esters of dimers and trimers having the following properties:

| viscosity, mm$^2$/s at: | |
| --- | --- |
| 40° C. | 99.9 |
| 100° C. | 13.9 |
| viscosity index | 141 |
| flow point (°C.) | −51. |

41. An oligomerization product produced by a process comprising oligomerizing a starting material consisting of $C_{16-22}$ fatty acids or $C_{1-12}$-alkyl esters thereof, said acids or esters containing polyunsaturated materials having conjugated double bonds, with an activated earth at a temperature of 100° to less than 160° C.

* * * * *